United States Patent
Azizian et al.

(10) Patent No.: US 10,283,220 B2
(45) Date of Patent: May 7, 2019

(54) SYSTEM AND METHOD FOR COORDINATED MOTION AMONG HETEROGENEOUS DEVICES

(71) Applicant: INTUITIVE SURGICAL OPERATIONS, INC., Sunnyvale, CA (US)

(72) Inventors: Mahdi Azizian, Santa Clara, CA (US); Jonathan M. Sorger, Belmont, CA (US); Simon P. Dimaio, San Carlos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 307 days.

(21) Appl. No.: 14/912,083

(22) PCT Filed: Aug. 14, 2014

(86) PCT No.: PCT/US2014/051027
§ 371 (c)(1),
(2) Date: Feb. 12, 2016

(87) PCT Pub. No.: WO2015/023831
PCT Pub. Date: Feb. 19, 2015

(65) Prior Publication Data
US 2016/0203282 A1 Jul. 14, 2016

Related U.S. Application Data

(60) Provisional application No. 61/866,949, filed on Aug. 16, 2013.

(51) Int. Cl.
*G05B 15/02* (2006.01)
*G16H 40/63* (2018.01)
*G06F 19/00* (2018.01)

(52) U.S. Cl.
CPC ............. *G16H 40/63* (2018.01); *G05B 15/02* (2013.01); *G06F 19/00* (2013.01); *G06F 19/3418* (2013.01); *G06F 19/3481* (2013.01)

(58) Field of Classification Search
CPC ............. G06F 19/3406; G06F 19/3418; G06F 19/3481; G05B 15/02; G05B 19/042; H05B 37/0227; B23P 19/066; B25B 23/14
See application file for complete search history.

(56) References Cited

U.S. PATENT DOCUMENTS

2004/0230334 A1    11/2004   Geismar et al.
2005/0273200 A1    12/2005   Hietmann et al.
(Continued)

FOREIGN PATENT DOCUMENTS

JP    2000300579 A    10/2000
JP    2004358564 A    12/2004
(Continued)

OTHER PUBLICATIONS

Noguchi N., et al., "Development of a Master-slave Robot System for Farm Operations," Computers and Electronics in Agriculture, Amsterdam, NL, vol. 44, No. 1, Jul. 31, 2004 (Jul. 31, 2004), pp. 1-19, XP055352989, ISSN: 0168-1699, DOI: 10.1016/j.compag. 2004.01.006.
(Continued)

*Primary Examiner* — Harry W Byrne
*Assistant Examiner* — Sultana Begum
(74) *Attorney, Agent, or Firm* — Haynes and Boone, LLP (57) ABSTRACT

A system and method of coordinated motion among heterogeneous devices includes a medical device with one or more movable elements and one or more processors. Any of the processors uses a shared interface to access services. The medical device requests a movement token from a token
(Continued)

service through the shared interface, receive the movement token from the token service, exchange configuration data, kinematic data, or planned motion data through the shared interface, plan a first motion for a first movable element of the movable elements based on the movement token and the configuration data, the kinematic data, or the planned motion data, and execute the first motion. In some embodiments, the movement token is selected from a group consisting of an exclusive-motion token, a master follow-me token, a slave follow-me token, a master collision-avoidance token, a slave collision-avoidance token, and a passive collision-avoidance token.

19 Claims, 4 Drawing Sheets

(56) References Cited

U.S. PATENT DOCUMENTS

| | | | |
|---|---|---|---|
| 2006/0148063 A1* | 7/2006 | Fauzzi | G01N 1/31 435/286.4 |
| 2008/0004904 A1 | 1/2008 | Tran | |
| 2009/0125084 A1 | 5/2009 | Juels et al. | |
| 2010/0161973 A1 | 6/2010 | Chin et al. | |
| 2011/0066282 A1 | 3/2011 | Bosscher et al. | |
| 2011/0191767 A1 | 8/2011 | Pinsky et al. | |
| 2013/0151739 A1 | 6/2013 | Smith | |
| 2015/0282106 A1* | 10/2015 | Xue | H04W 76/14 370/350 |

FOREIGN PATENT DOCUMENTS

| | | |
|---|---|---|
| JP | 2006192554 A | 7/2006 |
| JP | 2011224776 A | 11/2011 |
| JP | 2013504447 A | 2/2013 |
| WO | WO-2004104716 A1 | 12/2004 |

OTHER PUBLICATIONS

Partial Supplementary European Search Report for Application No. EP14836436.7, dated Mar. 24, 2017, 11 pages.

Spencer A., et al., "Collision Avoidance Techniques for Tele-operated and Autonomous Manipulators in Overlapping Workspaces," 2008 IEEE International Conference on Robotics and Automation. The Half-Day Workshop on: Towards Autonomous Agriculture of Tomorrow, IEEE—Piscataway, NJ, USA, May 19, 2008 (May 19, 2008), pp. 2910-2915, XP031340595, ISBN: 978-1-4244-1646-2.

Su L., et al., "Collaborative Assembly Operation between Two Modular Robots Based on the Optical Position Feedback," Journal of Robotics, vol. 2009, Jan. 31, 2009 (Jan. 31, 2009), pp. 1-8, XP055352990, ISSN: 1687-9600, DOI: 10.1155/2009/214154.

International Search Report and Written Opinion for Application No. PCT/US14/51027, dated Nov. 26, 2014, 9 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. 14836436.7, dated Jul. 5, 2017, 17 pages.

* cited by examiner

SYSTEM AND METHOD FOR COORDINATED MOTION AMONG HETEROGENEOUS DEVICES

RELATED APPLICATIONS

This application is a U.S. National Stage patent application of International Patent Application No. PCT/US2014/051027 (filed Aug. 14, 2014), the benefit of which is claimed, and claims priority to U.S. Provisional Patent Application No. 61/866,957 (filed Aug. 16, 2013), the disclosures of which are both hereby incorporated by reference in their entirety.

TECHNICAL FIELD

The present disclosure relates generally to interoperability among heterogeneous devices and more particularly to coordinated motion among heterogeneous devices.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

These electronic devices provide both advantages and challenges to the personnel operating them. Each of these electronic devices may be capable of providing large volumes of both accurate and precise data regarding patient conditions, the state of the electronic devices, and so forth. However, because each of these different electronic devices monitor and/or operate using different data and perform different tasks, they form a heterogeneous collection of medical devices. And despite the presence of programmable processors and microprocessors in many of these heterogeneous devices, the ability of these heterogeneous medical devices to share data and information and to coordinate their respective operations is often significantly underutilized.

In many cases, there is little to no exchange of data and information between the heterogeneous devices. One reason for this is that many of the heterogeneous medical devices in an operating room or interventional suite are provided by different vendors. Other reasons include differences between various models of devices and even the different tasks each of the medical devices is designed to perform. Consequently, many operating rooms and interventional suites are filled with heterogeneous medical devices that are not aware of each other and do not exchange data and information between themselves, much less exhibit any kind of significant interoperability. Instead, medical personnel are often expected to monitor and operate each of the devices independently or the devices must be used in such a way that they do not interfere with each other. For example, a computer-assisted surgical device may only be permitted in areas of the operating room where it won't interfere or collide with an imaging system also present in the operating room. Such a restriction may limit the functionality of both the computer-assisted surgical device and the imaging system.

One approach to supporting the exchange of data and information between heterogeneous devices and other forms of interoperability involves joint development efforts between the vendors or design teams of a single vendor. These efforts may include the development of custom hardware and/or software to permit two different heterogeneous devices to exchange data and information and to interoperate. These types of development efforts are often very time consuming and expensive and often require extensive testing and maintenance. They further provide only a limited solution to the larger interoperability problem because they only address issues between the two specific heterogeneous devices. The development work may not extend to other devices, even in the same product line, and likely will not extend to other types of devices or to devices from other vendors. These development efforts may further introduce complications associated with the exchange of intellectual property, such as trade secrets, and difficulty identifying the owner of the final product.

Accordingly, it is desirable to provide improved methods and systems for supporting interoperability between heterogeneous devices. It is also desirable to provide improved methods and systems for supporting coordinated motion among the heterogeneous devices.

SUMMARY

Consistent with some embodiments, a medical device includes one or more movable elements and one or more processors. Any of the one or more processors uses a shared interface to access services. The medical device is configured to request a movement token from a token service through the shared interface, receive the movement token from the token service, exchange configuration data, kinematic data, or planned motion data through the shared interface, plan a first motion for a first movable element of the movable elements based on the movement token and the configuration data, the kinematic data, or the planned motion data, and execute the first motion.

Consistent with some embodiments, a method of coordinated motion includes accessing a shared interface, requesting a movement token from a token service through the shared interface, receiving the movement token from the token service, exchanging configuration data, kinematic data, or planned motion data through the shared interface, planning a first motion for a movable element based on the movement token and the configuration data, the kinematic data, or the motion planning data, and executing the first motion.

Consistent with some embodiments, coordinated motion system includes a server including a shared interface for accessing one or more services including a token service, a first heterogeneous device coupled to the shared interface and including a first movable element, and a second heterogeneous device coupled to the shared interface and comprising a second movable element. The first heterogeneous device is configured to request a first movement token from the token service through the shared interface, receive the first movement token from the token service, receive configuration data, kinematic data, or planned motion data for the second movable element from a publisher service of the shared interface, plan a motion for the first movable element based on the first movement token and the configuration data, the position data, or the planned motion data, and execute the first motion. The second heterogeneous device is configured to request a second movement token from the token service through the shared interface, receive the second movement token from the token service, transmit the configuration data, the kinematic data, or the planned motion data for the second movable element to the shared interface using a blackboard service, and release the received second movement token.

BRIEF DESCRIPTION OF THE DRAWINGS

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1:
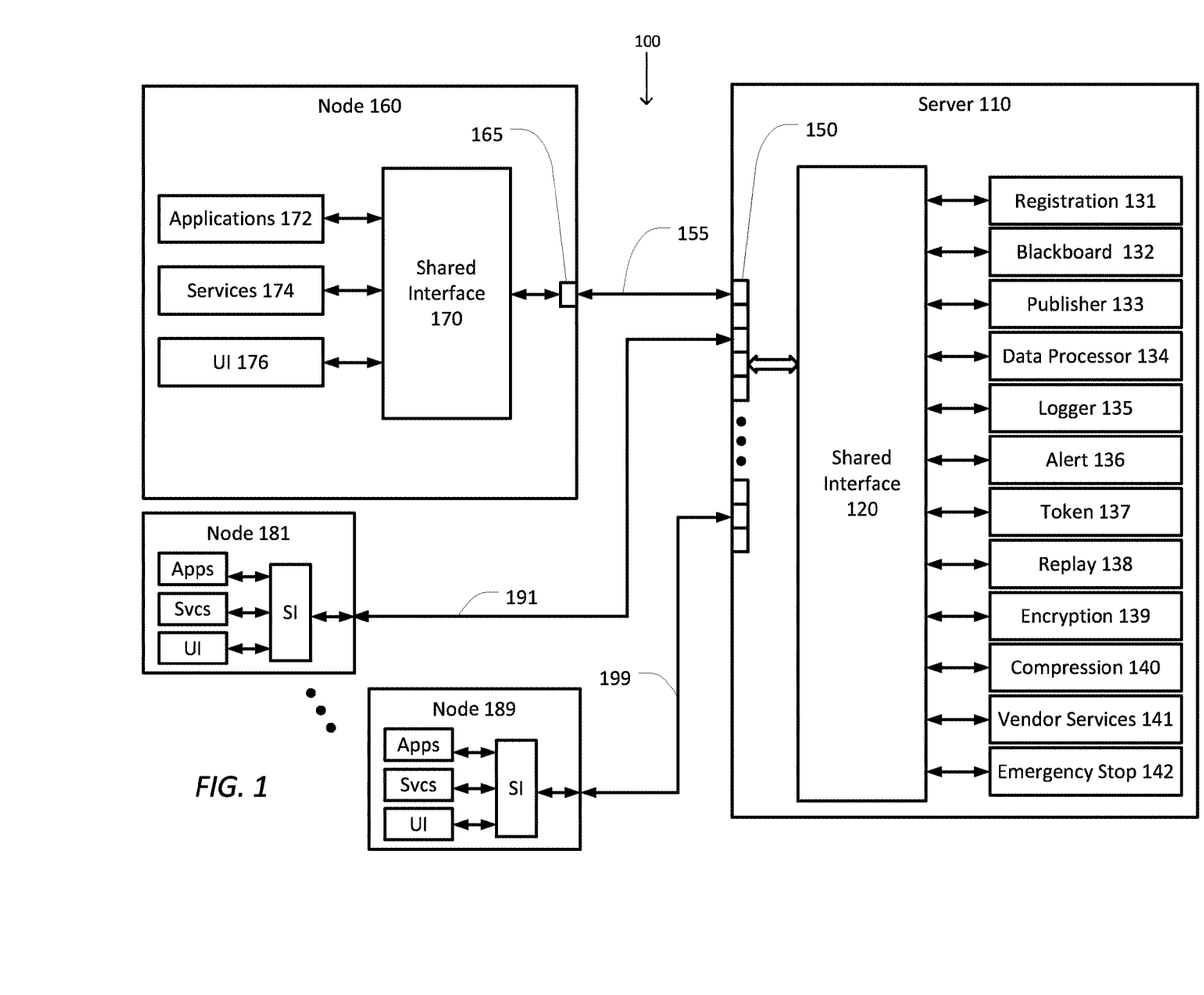
FIG. 1 is a simplified diagram of an interoperability system according to some embodiments.

FIG. 1 is a simplified diagram of an interoperability system 100 according to some embodiments. As shown in FIG. 1, interoperability system 100 includes a server 110 for acting as an interoperability point for interoperability system 100. Server 110 may be a workstation or any other kind of computing device, including one or more clustered computing devices, and as such it may be a stand-alone component or embedded in one or more medical devices. Although not shown in FIG. 1, server 110 may include one or more processors and memory. The memory may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Server 110 includes a shared interface 120 designed to support and standardize communication and interoperability between heterogeneous medical devices that are coupled to shared interface 120. The heterogeneous devices may include one or more devices that perform different tasks and/or may be provided by different vendors. In some examples, the heterogeneous devices may include two or more devices of the same type, model, and version. Shared interface 120 provides a known hardware and software interface that each of the heterogeneous devices may use. Shared interface 120 may further receive requests from the heterogeneous devices. In some examples, the requests may be generated by the heterogeneous devices and received by shared interface 120 using mechanisms such as application programming interface (API) calls, remote procedure calls, web services calls, message passing, and/or the like. Shared interface 120 may also transmit data and/or other information back to the heterogeneous devices to further support interoperability. In some examples, shared interface 120 may be implemented using a layered software stack and/or a combined hardware and software stack.

To support interoperability between the heterogeneous devices, server 110 may further include support for a flexible collection of service modules or services. In some examples, the services may include one or more of the following services, a registration service 131, a blackboard service 132, a publisher service 133, a data processing service 134, a logging service 135, an alert service 136, a token service 137, a replay service 138, an encryption service 139, a compression service 140, vendor services 141, an emergency stop service 142, and/or the like. Although only services 131-142 are shown in FIG. 1, this list of services 131-142 is illustrative only and not limiting. Any one or more of the services 131-142 may be omitted and/or other services not described may be added. Each of the services may add additional functionality to support interoperability and the services may be mixed and matched depending on the type and level of interoperability desired between the heterogeneous devices. In some examples, server 110 may also provide additional services not shown in FIG. 1. In some examples, services may be added and/or removed from server 110 by using one or more plug-ins supported by shared interface 120.

Registration service 131 includes support for registering and/or authenticating users and/or heterogeneous devices that use the other services, such as services 132-142, provided by server 110. In some examples, registration service 131 may provide a login mechanism using a username and password for limiting access to server 110 to only authorized users and/or heterogeneous devices. In some examples, upon successful registration, an authenticated user and/or heterogeneous device may be provided with one or more keys and/or session identifiers. The one or more keys and/or session identifiers may be used to identify the user and/or heterogeneous device with the other services 132-142 provided by server 110. The one or more keys and/or session identifiers may also be used to encrypt and/or decrypt data and other information exchanged between the users and/or the heterogeneous devices and server 110 and/or data stored in server 110.

In some examples, registration service 131 may further maintain one or more access control lists used by shared interface 120 and/or services 132-142 to limit access to services 132-142. In some examples, the process of registration with registration service 131 may further include identifying a type of heterogeneous device connecting to server 110. The type of heterogeneous device may include information such as a vendor and model number of the heterogeneous device, a firmware version number, a classification for the heterogeneous device, and/or the like. The classification may include categories such as computer-assisted medical device, imaging device, cardiac monitor, and/or the like. In some examples, registration service 131 may provide registration at the application level rather than the device level so that different applications supported by the same heterogeneous device may have different levels of access to server 110 and services 132-142. In some examples, registration service 131 may update one or more data structures necessary to manage its functionality.

Blackboard service 132 provides a memory area that may be shared among the heterogeneous devices. Each of the heterogeneous devices registered with the server 110 and the shared interface 120 may use blackboard service 132 to record data and information that may then be shared with other heterogeneous devices. For example, a computer-assisted surgical device and/or an imaging system may supply information associated with no-fly zones that represent areas and/or volumes in which entry is not permitted, component positioning, and/or motion path planning to blackboard service 132 so that other movable devices may coordinate their movements accordingly.

In some embodiments, blackboard service 132 may store data in the shared memory area using a key-value pair approach. When a heterogeneous device provides data to blackboard service 132, the data may be associated with a unique key that may be used to retrieve the data later. The key may be supplied by the heterogeneous device supplying the data, or it may be generated by blackboard service 132. In some examples, data exchanged between blackboard service 132 and the homogeneous devices may be exchanged using one or more protocols including hypertext transport protocol (HTTP), user datagram protocol (UDP), extensible markup language (XML), health level 7 (HL7), digital imaging and communication in medicine (DICOM), Controller Area Network (CAN), Fieldbus (IEC61158), Process Field Bus (Profibus), and/or the like. In some examples, blackboard service 132 may further encrypt and/or compress one or more data items in the shared memory for security purposes. In some examples, blackboard service 132 may rely on encryption service 139 and/or compression service 140 to perform encryption/decryption and/or compression/decompression. In some examples, blackboard service 132 may use the one or more access control lists maintained by registration service 131 to limit access to some of the data in the shared memory to a subset of applications and/or other heterogeneous devices. In some examples, blackboard service 132 may also provide support for locking of data in the shared memory that may temporarily make portions of the data in the shared memory unavailable to other heterogeneous devices.

Publisher service 133 provides a publish-subscribe mechanism for proactively sharing data and information between the heterogeneous devices. Using publisher service 133, heterogeneous devices may subscribe to notifications and/or callbacks associated with other data and information published to publisher server 133 by other heterogeneous devices. For example, a heterogeneous device may request to be notified or receive a callback whenever an update is made to data stored in the shared memory of blackboard service 132, such as when an imaging device makes a new image available. In some examples, publisher service 133 may support conditional checks on the updated data before sending out a notification. In some examples, the conditional checks may include one or more Boolean tests based on range checks, locking status, and/or other tests based on the values or status of data. As with blackboard service 132, publisher service 133 may additionally support encryption, compression, and/or access control lists, or it may rely on other services such as encryption service 139 and/or compression service 140 to provide this functionality.

Data processing service 134 provides scripting and post-processing of data supplied to shared interface 120. In some examples, data processing service 134 may perform data fusion, aggregation, and/or statistical analysis of data and information stored using blackboard service 132. The data fusion and statistical analysis may, for example, include computing a running and/or weighted average and/or estimate noise parameters of numerical values stored using blackboard service 132. In some examples, data processing service 134 may support a scripting language allowing other heterogeneous devices to supply simple and/or complex scripts to be executed on stored data that may additionally be used in conjunction with the notifications and callbacks of publisher service 133. In some examples, data processing service 134 may receive custom processing scripts from the heterogeneous devices that data processing service 134 may use on the stored or parameterized data.

In some embodiments, data processing service 134 may reduce bandwidth requirements between server 110 and the heterogeneous devices by aggregating data centrally so that only the aggregated data is distributed among the heterogeneous devices. In some embodiments, data processing service 134 may additionally streamline the aggregation of data from many different heterogeneous devices.

Logging service 135 provides the ability to log data and/or events provided by the heterogeneous devices. Using one or more logs, logging service 135 may be configured to record data and events along with timestamps. For example, a log may be configured to record updates made to specific data items stored using blackboard service 132 and/or to record updates made by specific heterogeneous devices. In some embodiments, logging service 135 may also support a user interface (not shown) for configuring logging service 135, accessing recorded logs, and/or managing recorded logs. In some examples, the user interface may access logging service 135 remotely from a separate computer or workstation. In some embodiments, logging service 135 may also support time synchronization between server 110 and the heterogeneous devices to ensure that timestamps being recorded across the one or more logs consistently reflect the actual time of data updates and events. In some examples, logging service 135 may exchange one or more synchronization messages with the heterogeneous devices to more accurately model effects associated with latency associated with processing and/or communication delays between server 110 and the heterogeneous devices and/or clock drift. In some examples, logging service 135 may use compression, such as that provided by compression service 141 to reduce the size of the recorded logs.

In some embodiments, logging service 135 may record the logs in memory and/or some type of persistent storage device. In some examples, the logs may be recorded using a disk drive or similar storage medium located in server 110. In some examples, the logs may be recorded using a disk drive or storage medium located in a separate workstation (not shown).

In some embodiments, logging service 135 may also make the one or more logs available for offline use. In some examples, the one or more logs may be used to evaluate, test, and/or debug individual heterogeneous devices and/or to coordinate among the heterogeneous devices. In some examples, the one or more logs may be data mined and/or subject to analysis to evaluate, for example, the efficiency of a heterogeneous device. In some examples, the one or more logs may be used to synthesize one or more models and/or atlases based on the logged information, such as representative and/or test trajectories of movable devices. In some examples, the one or more logs may be made available to replay service 138.

Alert service 136 provides the ability to send synchronous and/or asynchronous notifications to the heterogeneous devices. Unlike publisher service 133, alert service 136 is not necessarily restricted for use with data updates. In some embodiments, alert service 136 may be used to share asynchronous notifications associated with interrupts, exceptions, emergency stop events, and/or other events between the heterogeneous devices. For example, an oxygen sensor may use alert service 136 to notify other heterogeneous devices, such as a cautery tool, that an unsafe level of oxygen is detected. In some embodiments, alert server 136 may be used to share synchronous notifications, such as those associated with a time keeping system that issues periodic time synchronization messages and/or heartbeat messages.

Token service 137 provides a system for sharing coordination tokens among the heterogeneous devices. Using token service 137, heterogeneous devices may request and release coordination tokens. As needed, heterogeneous devices may be blocked from further action when they cannot obtain the desired coordination tokens. Coordination tokens may include mutually exclusive (MUTEX) tokens, multiple use tokens, and/or special-purpose tokens as needed by the heterogeneous devices. In some examples, a MUTEX token may be used to avoid race and/or deadlock conditions between two heterogeneous devices, such as may occur when two movable devices are using collision avoidance strategies and only one movable device at a time should be moving. In some examples, multiple use tokens may be issued to a limited number of heterogeneous devices so that a shared resource is made available only to the number of heterogeneous devices that the shared resource may support. In some embodiments, special-purpose tokens may be used to coordinate specific activities among the heterogeneous devices.

In the context of coordinated movement, the special-purpose tokens may include exclusive-motion tokens, follow-me tokens, collision-avoidance tokens, and/or the like. An exclusive-motion token may be used when only a single movable device is permitted to move. In some examples, a movable device may be any device capable of autonomous and/or semi-autonomous movement of one or more elements coupled to the device. In some examples, a movable device may include a device where either part or all of the device may be moved. Only the movable device holding the exclusive-motion token may be allowed to move. In some examples, the movable device holding the exclusive-motion token may use positioning data from other devices that is stored using blackboard service 132 to plan a motion path that is collision free. A follow-me token may be used when one of two or more movable devices is executing a movement that the other movable device or devices should follow. In some examples, the movable device or devices holding a follow-me token may use motion path planning and/or other positioning data that is stored using blackboard service 132 to plan a compliant trajectory. A collision-avoidance token may be used when a primary movable device needs to execute a motion and one or more other secondary movable devices should move out of the way of the primary movable device as it moves. In some examples, the follow-me token and the collision-avoidance token may involve multiple sub-tokens, an exclusive master token held by the primary movable device, and other sharable slave tokens held by the secondary movable devices. In some examples, the secondary movable device or devices may use path planning and/or other positioning data from the primary movable device that is stored using blackboard service 132 to plan a compliant and/or collision-free trajectory. In some embodiments, token service 137 may be used by one movable device to assign a specific movement token to another movable device. In some examples, the assignment of movement tokens may be used by a movable device holding a master token to assign one or more slave tokens to corresponding one or more other movable devices as necessary. In some examples, a movable device planning to perform a motion may assign a passive collision-avoidance token on one or more other movable devices. The passive collision-avoidance token or tokens may be used to restrict and/or prohibit motion in the other movable device or devices as well as request that the other movable device or devices periodically report their current position. In some examples, the movable device requesting assignment of a movement token may wait for confirmation of the assignment before performing any motion. In some examples, token service 137 may also use alert service 136 to coordinate the issuance and/or assignment of the various sub-tokens.

Replay service 138 provides a system for replaying data streams and/or events from one or more logs. In some embodiments, replay service 138 may be used to review and/or recreate a surgery or other procedure in a simulated environment for training and/or evaluation purposes. In some embodiments, replay service 138 may be used in a system to emulate one or more of the heterogeneous devices as playback devices. In some examples, a computer-assisted surgical device may be used in an environment with a simulated imaging device for the purposes of procedure planning and the like. The logged series of images from the imaging device may be replayed by replay service 138 using the recorded timestamps for sequencing while the computer-assisted surgical device is operated live. In some examples, the playback imaging device may be used with replayed trajectory data of the computer-assisted surgical device to plan the best trajectory a movable medical imaging device can take for capturing a desired image of a patient while avoiding collision with the computer-assisted surgical device. In some examples, replay service 138 may be used with previously logged trajectory data to test and/or evaluate follow-me or collision-avoidance algorithms without the risk of actual collisions between movable devices and/or danger to an actual patient. In some embodiments, replay service 138 may also replay synthetic data based on models from logged data and/or simulations from vendors. In some embodiments, replay service 138 may be used in conjunction with a mix of live, recorded, simulated, and/or synthetic heterogeneous devices.

Encryption service 139 provides a system for decoupling encryption and decryption processes and/or algorithms from the other services coupled to shared interface 120. By decoupling encryption and decryption from the other services, users of shared interface 120 may install and/or operate different encryption and decryption processes and algorithms without having to embed that functionality into one of the other services. Encryption service 139 may provide any kind of encryption and decryption such as symmetric key encryption, public-key encryption, private-key encryption, and/or the like. Encryption services 139 may further provide data integrity services such as check summing, CRC coding, MD5, and/or other such services.

Compression service 140 provides a system for decoupling compression and decompression processes and/or algorithms from the other services. By decoupling compression and decompression from the other services, users of shared interface 120 may install and/or operate different compression and decompression processes and algorithms without having to embed that functionality into one of the other services. Compression services 140 may provide any kind of compression and decompression including lossless compression and decompression such as Lempel-Ziv-Welch (LZW) compression, and/or the like and/or lossy compression such as JPEG, MPEG, and/or the like.

Vendor services 141 provides a system for allowing the heterogeneous devices to make additional services available among themselves. In some embodiments, vendor services 141 may provide registration for sharing the existence of available services in the heterogeneous devices. In some examples, vendor services 141 may include a registry or catalog of available services including interface specifications so that other heterogeneous devices may use the available services. In some examples, the interface specifications may include definitions similar to those used to publish and share web services. In some examples, vendor services 141 may provide locating and/or forwarding services that may couple heterogeneous devices wanting to use an available service to the heterogeneous device hosting the service.

Emergency stop service 142 provides support for safe shutdown and/or support for other graceful failure operations among the heterogeneous devices using server 110 and/or shared interface 120. In some examples, emergency stop service 142 may work in cooperation with alert service 136 to either monitor activity among the other services and/or the heterogeneous devices or to provide emergency stop and/or other failure alerts to the other services and/or the heterogeneous devices. For example, emergency stop service 142 may be used to transmit a stop moving alert to each of the heterogeneous devices that are capable of movement. Although not shown in FIG. 1, in some examples, emergency stop service 142 may be coupled to one or more dead-man switches, watchdog timers, watchdog relays, and/or other emergency stop and watchdog devices. In some examples, emergency stop service 142 may be further coupled to one or more shared safety circuits (not shown) with dedicated wiring to each of the heterogeneous devices to share emergency stop signals with each of the heterogeneous devices. In some examples, the shared safety circuits may include both primary and backup secondary circuits.

Server 110 further includes a plurality of hardware ports 150 for coupling server 110 to the heterogeneous devices. In some examples, one or more of the hardware ports 150 may provide support for standardized hardware interfaces such as universal serial bus (USB), firewire (IEEE 1394), RS232, RS485, CAN, Fieldbus, Profibus, inter-integrated circuit (I2C), and/or the like. In some examples, one or more of the hardware ports 150 may provide support for coupling server 110 to local area networks (LANs) such as Ethernet and/or wide-area networks (WANs) such as an internet. In some examples, one or more of the hardware ports 150 may be provided through custom-designed and/or vendor-specific interface cards that may be installed in server 110 using slots that support standards such as peripheral component interconnect express (PCIe), ExpressCard, and/or the like.

As shown in FIG. 1, interoperability system 100 further includes a link 155 coupling one of the hardware ports 150 of server 110 to an exemplary heterogeneous device as depicted by a node 160 at a port 165. In some embodiments, data transferred using link 155 may be encrypted. Like server 110, node 160 may include one or more processors and memory. Additionally, port 165 may be similar to any of the ports 150. In some embodiments, node 160 may be any of many types of heterogeneous devices including an imaging device, a picture archiving and communication system (PACS) station, a computer-assisted surgical or interventional device, a focal interventional device, a localization device, a positioning device, a tracking device, a monitoring device, a surgical table, a smart floor or wall supporting navigation, display, and/or other technologies, a camera, a range sensor, an environment sensor, a tracking device, and/or the like. The focal interventional device may include any diagnostic device and/or therapy device, including a biopsy device, a tissue sampling device, and/or the like. The imaging device may be an ultrasound, x-ray, CT, MRI device, a gamma probe, and/or the like. The monitoring device may include a cardiac monitor, a respiration monitor, and/or the like. The range sensor may include a SONAR device, a LIDAR device, and/or the like. The environment sensor may include a heat sensor, a pressure sensor, a humidity sensor, an oxygen sensor, and/or the like. In some examples, the tracking device may include one or more tracking technologies based on vision, electromagnetics, RFID, ultrasonics, articulated mechanical systems, and/or the like.

Like server 110, node 160 includes a shared interface 170. For example, shared interface 170 may be using APIs and/or software development kits (SDKs) that permit node 160 to take advantage of shared interface 120 and the services 131-142 of server 110. In some examples, shared interface 170 may be a local version of shared interface 120.

Node 160 further includes one or more applications 172 that use shared interface 170 to access shared interface 120 and services 131-142. The applications 172 permit node 160 to be an active participant in interoperability system 100. The one or more applications 172 may, for example, register with server 110 using registration service 131, use blackboard service 132 to exchange data and information with other heterogeneous devices and nodes, enable logging using logging service 135 and/or the like. In other examples, when node 160 is a movable device, the applications 172 may include motion planning and execution algorithms that use the specialized tokens from token service 137 and data from blackboard service 132 to coordinate motion with one or more other movable devices.

Node 160 may further include one or more services 174 that also use shared interface 170. In some embodiments, the services 174 may include services that asynchronously or synchronously share data and information from node 160 to blackboard service 132 to be shared with other heterogeneous devices and/or node. In some examples, the services 174 may include a service that sends new images taken by an imaging device to blackboard service 132 for sharing. In some examples, the services 174 may include a service that synchronously updates the location coordinates of a movable device.

In some embodiments, the services 174 may include shared services that node 160 may make available to other heterogeneous devices and/or nodes in interoperability system 100 using, for example, vendor services 141. In some examples, the shared services may include any of the services 131-142 and/or additional services being provided by node 160. In some examples, the shared services of node 160 may include access to parameterized processing scripts that preprocess data before it is sent for sharing to blackboard service 132. As an example, a parameterized processing script in an imaging device may accept parameters for a proprietary imaging processing algorithm that may be applied to images before they are shared. Using this parameterized processing script, other heterogeneous devices and/or nodes may request customized versions of images.

Node 160 may also include support for a user interface 176. User interface 176 may be used to manage and/or control applications 172 and/or services 174. In some examples, user interface 176 may be used to control which services 174 are available to other heterogeneous devices and/or nodes in system 100. In some examples, user interface 176 may be used to control the rate at which data is sent to blackboard service 132. In some examples, user interface 176 may be used to control which data and/or events are to be logged by logging service 135. In some embodiments, user interface 176 may be a graphical user interface. In some embodiments, user interface 176 may be accessed using a control panel and/or monitor screen, such as a touch screen, on node 160. In some embodiments, user interface 176 may be remotely accessed using a terminal, a workstation, a surgical console, and/or the like coupled to node 160 over a network.

As further shown in FIG. 1, interoperability system 100 may further include any number of nodes and/or heterogeneous devices. Two such additional nodes are shown as nodes 181 and 189, which represent a range of nodes from node 181 to node 189. Like node 160, node 181 includes a version of the shared interface as well as applications, services, and/or a user interface. Node 181 is coupled to server 110 using link 191. Similarly, node 189 includes a version of the shared interface as well as applications, services, and/or a user interface and is coupled to server 110 using link 199. Each of nodes 181-189 represents a heterogeneous device and may be different from or the same model as any of the other nodes 160 and 181-189, such that it is possible that nodes 160 and 181-189 may include two or more medical devices that are the same.

Figure 2:
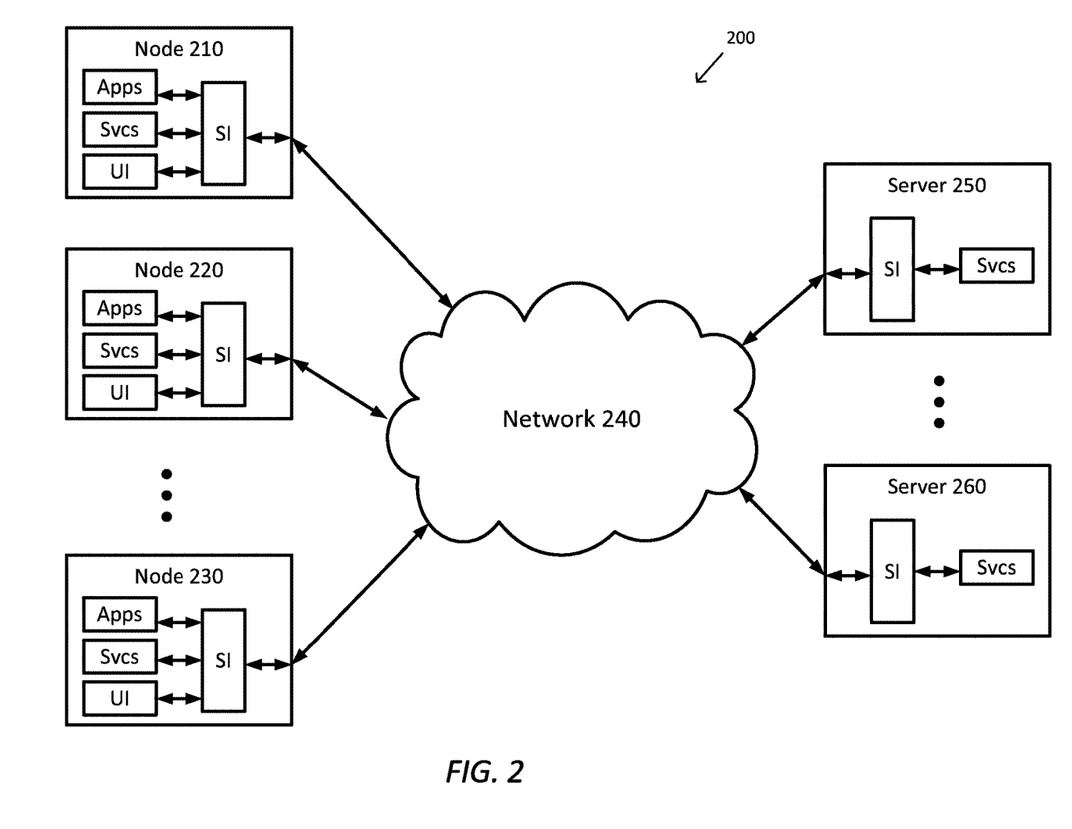
FIG. 2 is a simplified diagram of another interoperability system according to some embodiments.

FIG. 2 is a simplified diagram of another interoperability system 200 according to some embodiments. As shown in FIG. 2, interoperability system 200 includes several heterogeneous medical devices or nodes 210-230. Although three nodes are depicted in interoperability system 200, interoperability system 200 may include any number of nodes. Nodes 210-230 are similar to nodes 160 and 181-189. Each of the nodes 210-230 may include a version of the shared interface, applications, services, and/or a user interface as described above.

Each of the nodes 210-230 is coupled using a network 240 to servers 250 and 260. Network 240 may be any kind of network, including a LAN and/or a WAN. Servers 250 and 260 may be similar to server 110 and may each include a version of shared interface 120 and/or services 131-142. Although two servers are depicted in interoperability system 200, interoperability system 200 may include any number of servers, including no servers when the shared interface 120 is distributed across nodes 210-230. Depiction of servers 250 and 260 underscores the flexible nature of the shared interfaces 120 and 170 and interoperability system 200 as the services 131-142 and 172 may potentially be hosted in any combination on the nodes 210-230 and servers 250 and 260. In some embodiments, servers 250 and 260 may be omitted and the services 131-142 may be hosted entirely on node 210 or on any combination of the nodes 210-230. In some embodiments, any of the nodes 210-230 may be combined into the same workstation or cluster as any of the servers 250-260. In some embodiments, server 260 may be a mirror of server 250 providing backup and/or fail over support for server 250. In some embodiments, services 131-142 may be duplicated among servers 250 and 260. In some examples, server 250 may include a version of logging services 135 that is used for logging certain types of data, and server 260 may include another version of logging services 135 that is used for logging other types of data. In some embodiments, interoperability system may include only a limited server or hub that may provide only registration service 131 and vendor services 141, with vendor services 141 being used to locate and direct service requests to the nodes 210-230 hosting the other services 132-140 and/or 142.

Figure 3:
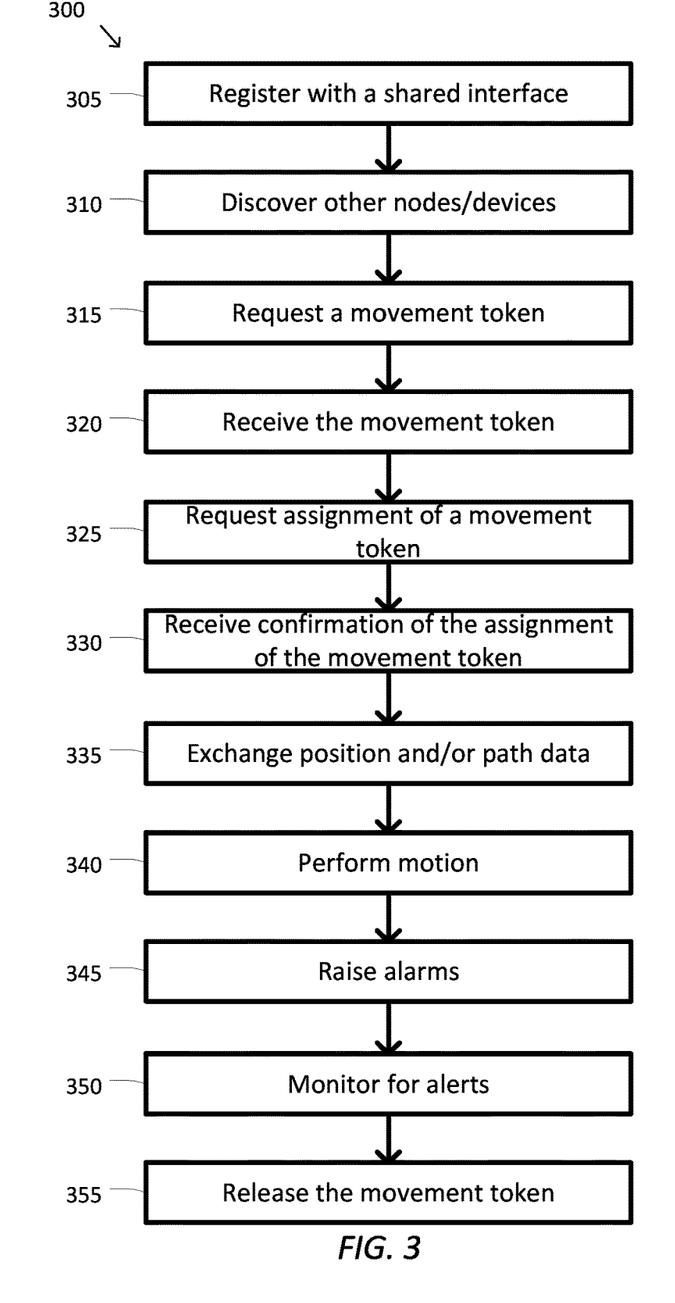
FIG. 3 is a simplified diagram of a method of performing coordinated motion in a movable device according to some embodiments.

FIG. 3 is a simplified diagram of a method 300 of performing coordinated motion in a movable device according to some embodiments. One or more of the processes 305-355 of method 300 may be implemented, at least in part, in the form of executable code stored on non-transient, tangible, machine readable media that when run by one or more processors (e.g., one or more processors in nodes 160, 181-189, and/or 210-230 and/or in the servers 110, 250, and/or 260) may cause the one or more processors to perform one or more of the processes 305-355. In some embodiments, the method 300 may be performed by an application, such as one of the applications 172.

At a process 305, a movable device registers with a shared interface. In order to receive tokens and data used to perform coordinated motion, the movable device may register itself with a shared interface, such as shared interface 120. For example, the movable device may make a registration request to registration service 131. In some examples, the movable device may receive a key and/or a session identifier used to identify the movable device with the shared interface. In some embodiments, the movable device may additionally provide information that identifies the type of device it is and may further provide configuration, geometric, and/or kinematic information regarding its motion. In some examples, this may include providing one or more geometric and/or kinematic models of the movable device in the form of services, such as the services 174, that one or more other heterogeneous devices, nodes, and/or movable devices may use to discover a current and/or potential future volume that may be occupied by the movable device.

At a process 310, the movable device may discover one or more other nodes and/or movable devices. For example, the movable device may use the shared interface to access a list and/or other data structure with the one or more other nodes and/or movable devices of interest. In some examples, blackboard service 310 may store the list or data structure with the one or more other nodes and/or movable devices that the movable device may request using, for example, a universally recognized and/or standardized key. In some examples, based on the list of the one or more other nodes and/or movable devices the movable device may be able to determine the one or more types of coordinated motion that are possible and/or desirable.

At a process 315, the movable device requests a movement token. In a system with multiple movable devices, the movable device should hold or possess a movement token before undertaking any motion. This may be an important safety step to prevent collisions with the one or more other movable devices and/or to avoid danger to a patient and/or other personnel in the room with the movable device. In some examples, the movement token may be requested using token service 137. In some examples, the movement token may be a special-purpose token such as an exclusive-motion token, a follow-me token, a collision-avoidance token, and/or the like. In some examples, when the movable device desires to initiate motion it may request an exclusive-motion token, a master follow-me token, and/or a master collision-avoidance taken. In some examples, when the movable device desires to provide compliant motion and/or collision free motion, the movable device may request a slave token.

At a process 320, the movable device may receive the movement token. The movement token received may be based on the movement token requested during process 315.

In some examples, the movement token is received from token service 137. In some examples, the movable device may wait at process 320 until the movement token is received. In some embodiments, when the multiple movable devices can never have intersecting volumes, the movable device may receive an exclusive-motion token that allows the movable device to make unrestricted motion. In some embodiments, the movable device may receive multiple movement tokens placing multiple constraints on the movable device. For example, the movable device may receive a slave follow-me token to follow another movable device while also receiving a slave collision-avoidance token to avoid collisions with one or more other movable devices. In some examples, an aggregate of the one or more received movement tokens determines the motion behavior of the movable device. In some examples, the movable device may not receive the requested movement token for some time due to multiple pending requests for conflicting tokens made by the other movable devices. In some examples, multiple requests for conflicting tokens may be resolved using a priority system using a first-come first-served strategy, a predefined priority model, a custom priority model, and/or the like.

At a process 325, the movable device may request assignment of a movement token to one or more other movable devices. In some examples, to provide more safety and/or certainty during movement, the movable device may request that one or more specific types of movement tokens be assigned to one or more other movable devices discovered during process 310. In some examples, when the movable device receives a master movement token during process 320, the movable device may request that one or more corresponding slave movement tokens be assigned to the one or more other movable devices. In some examples, the movable device may request the assignment of one or more passive collision-avoidance tokens to the one or more other devices not holding a slave movement token, to help ensure that the movable device receives up to date position information from the one or more other movable devices during a process 335. By using process 325, the movable device may take more proactive control of coordinated motion among the one or more other movable devices.

At a process 330, the movable device receives confirmation of the assignment of the movement token. After requesting assignment of a movement token, the movable device may wait until it receives confirmation that the one or more other movement devices confirm the receipt of their corresponding movement tokens before performing any motion during a process 340.

At the process 335, the movable device exchanges position and/or path data with the one or more other movable devices. In some embodiments, irrespective of the movement token held by the movable device, the movable device may periodically send updates of its position and/or kinematic data using blackboard service 132. In some examples, these updates may be provided using a service such as one of the services 174. This allows the one or more other devices to monitor the motion of the movable device. In some examples, the movable device may share data describing the volume the movable device currently occupies. In some examples, the movable device may share data describing a circumscribing volume about the movable device that includes a buffer zone. In some examples, either of these volumes may describe a no-fly zone associated with the movable device. In some examples, the movable device may share moving joint parameters that a script accessible using data processing service 134 and/or vendor services 141 may be used to convert the joint parameters into the no-fly zone. In some examples, the movable device may share future path information, such as a planned motion, that allow the one or more other movable devices to comply with corresponding one or more slave follow-me and/or slave collision-avoidance tokens. In some examples, when the movable device holds a slave follow-me, a slave collision-avoidance, a passive collision-avoidance, and/or a similar token, the movable device may use blackboard service 132 to receive no-fly, position, and/or planned motion data on the one or more other movable devices and/or use publisher service 133 to receive updates on the no-fly, position, and/or path data. In some examples, the movable device may issue one or more requests that one or more of the other movable devices provide a position and/or planned motion update. In some examples, the position and/or path data may be associated with one or more energy beams and/or one or more energy fields being manipulated by the movable device. In some embodiments, the movable device may exchange force data with the one or more other movable devices. In some examples, the force data may include data associated with force, torque, pressure, and/or other static and/or dynamic characteristics of the movable device and/or the one or more other movable devices.

At the process 340, the movable device may perform motion. Based on the type of movement token or tokens held and the no-fly, position, and/or path data known about the one or more other movable devices, the movable device may plan and execute motion for one or more movable elements such as an articulated arm. In some examples, when the movable device holds a slave follow-me token, the movable device may plan and execute a motion compliant with the path shared by the other movable device holding the master follow-me token. In some examples, when the movable device holds a slave collision-avoidance token, the movable device may plan and execute a collision free path that avoids the no-fly, position, and/or path data shared by the other movable device holding the master collision-avoidance token. In some embodiments, motion planning among the movable devices may be centralized using a service such as data processing service 134 and/or a service 174 in one of the other movable devices. In some examples, the centralized motion planning service may make available a combined no-fly zone including one or more volumes occupied by each of the one or more other movable devices. In some examples, the performed motion may be associated with the one or more energy beams and/or the one or more energy fields.

At a process 345, the movable device may raise an alarm. For example, when the movable device is not able to comply with a slave token and/or must move despite not holding a movement token, the movable device may raise an alarm. In some examples, the movable device may use alert service 136 to notify the one or more other movable devices of its inability to comply with the movement token it holds. In some embodiments, the movable device may further raise an alarm based on position, path, and/or other data received from other movable devices during process 335. In some examples, the alarm may be related to observations the movable device may make about the positioning and/or motion of the other movable devices.

At a process 350, the movable device may monitor for alerts. For example, when the movable device holds an exclusive-motion token and/or a master token, the movable device may monitor for alerts that indicate that one of the other movable devices may not be able to comply as expected. In some examples, one or more alerts may result from an alarm raised during a corresponding process 345 in one of the other movable devices. In some examples, the movable device may monitor for alerts using alert service 136. In some embodiments, data processing service 134 and/or a custom movement service may be used in conjunction with alert service 136. In some examples, a script may be used to generate one or more special alerts for the movable device. In some examples, the script may request that an alert be issued whenever another movable device leaves and/or enters a defined volume. In some examples, the defined volume may be a sphere defined by a center and radius, a polyhedral volume defined by a convex hull, and/or other and possibly more complex volumes. In some examples, the script may request that an alert be issued whenever any other movable device performs any motion.

At a process 355, the movable device may release the movement token. When the movable device no longer desires to perform movement, it may release the movement token it received during process 320. In some examples, by releasing the movement token, the movable device may trigger one or more alerts that notify the one or more other movable devices that the token has been released. In this way, the one or more other movable devices holding corresponding slave tokens may be notified that they no longer need to comply with a slave follow-me and/or a slave collision-avoidance token. Upon release of an exclusive-motion token and/or a master movement token, one or more other movable devices that requested these movement tokens during their corresponding process 315 may receive the requested movement token during the corresponding process 320. In some examples, the movable device may release the movement token based on a request received from a user and/or another movable device.

Figure 4:
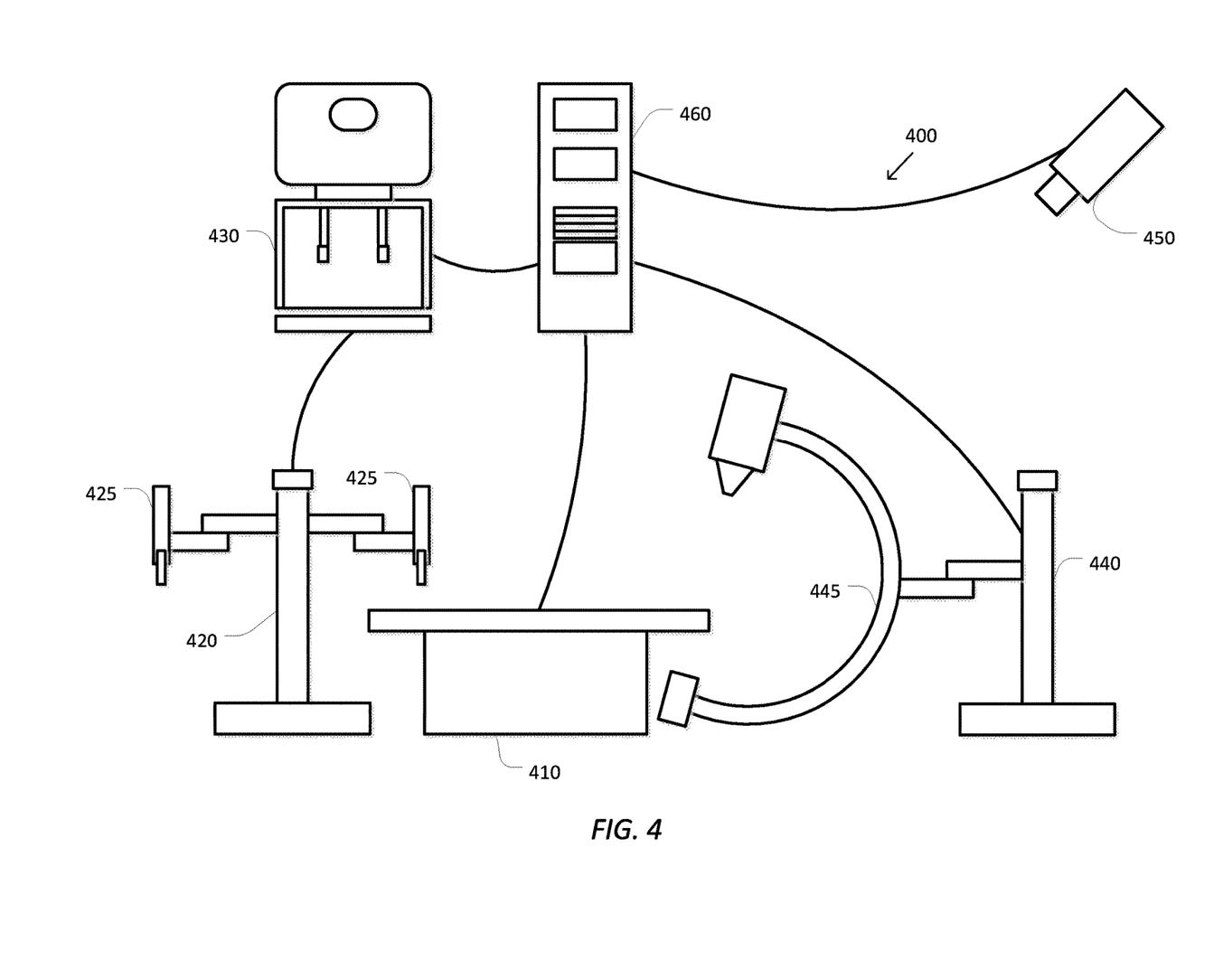
FIG. 4 is a simplified diagram of a coordinated motion system according to some embodiments.

FIG. 4 is a simplified diagram of a coordinated motion system 400 according to some embodiments. As shown in FIG. 4, coordinated motion system 400 may be found in an operating room and/or an interventional suite. Coordinated motion system 400 includes a patient cart and/or surgical table 410. Surgical table 410 may be a movable device. In some examples, surgical table 410 may perform movement in any one of its degrees of freedom. In some examples, surgical table 410 may be adjustable in height to account for the height of doctors and/or nurses performing a procedure on a patient and/or to account for the height and/or size of one or more other devices in the vicinity of the surgical table 410. In some examples, surgical table may move laterally and/or adjust roll, pitch, and/or yaw as needed to place the patient in a suitable posture to support the current surgery and/or procedure.

Coordinated motion system 400 also includes a computer-assisted surgical device 420. Computer-assisted surgical device 420 may include one or more movable elements or articulated arms 425 for supporting surgical instruments, imaging devices, and/or the like. Computer-assisted surgical device 420 is further coupled to surgeon console 430, which may include one or more master controls for operating the computer-assisted surgical device 420 and/or the one or more articulated arms 425. In some embodiments, computer-assisted surgical device 420 and surgeon console 430 may correspond to a da Vinci® Surgical System commercialized by Intuitive Surgical, Inc. of Sunnyvale, Calif. In some embodiments, computer-assisted surgical devices with other configurations, fewer or more articulated arms, and/or the like may be used with coordinated motion system 400. In some embodiments, computer-assisted surgical device 420 may be mounted to surgical table 410 rather than being free-standing as depicted in FIG. 4.

Coordinated motion system 400 may further include an imaging device 440. Imaging device 440 includes an imaging subsystem 445 that may be used to take one or more diagnostic images of a patient located on surgical table 410. Imaging device 440 and imaging subsystem 445 may include one or more movable elements necessary to position the imaging subsystem 445 about the patient to take the desired one or more diagnostic images. Although imaging device 440 in FIG. 4 is depicted with imaging subsystem 445 characterized as a C-arm, other types of imaging device 440 are possible in coordinated motion system 400. In some embodiments, imaging subsystem 445 may include a donut-shaped bore such as an MR-bore, an articulated arm with a probe, one or more articulated arms, and/or the like. In some embodiments, imaging device 440 may be mounted to surgical table 410 rather than being free-standing as depicted in FIG. 4.

Coordinated motion system 400 may further include a motion tracking system 450. Motion tracking system 450 may include one or more tracking devices that can track the position of one or more devices and/or one or more personnel in the vicinity of the coordinated motion system 400. In some examples, the tracking devices may include one or more tracking technologies based on vision, electromagnetics, RFID, ultrasonics, articulated mechanical systems, and/or the like. In some examples, motion tracking system 450 may track one or more registration points on the surgical table 410, the computer-assisted surgical device 420, the surgeon console 430, and/or the imaging device 440 as well as those on one or more other objects and/or one or more personnel. Based on the tracking data collected by motion tracking system 450, motion tracking system 450 may be able to monitor the position of one or more devices, raise one or more alerts, such as imminent collision alert, and/or allow the use of coordinated motion system 400 with one or more devices and/or one or more personnel that are not able to use the coordinated motion features such as the shared interface and/or token, alert, and/or other services. In some examples, motion tracking system 450 may create one or more virtual movable devices for each object and/or person being tracked. As with other movable devices, motion tracking system 450 may provide position and/or path updates for each of the one or more virtual movable devices.

The surgical table 410, the computer-assisted surgical device 420, the surgeon console 430, the imaging device 440, and the motion tracking system 450 may each be heterogeneous devices that include features similar to those found in nodes 160, 181-189, and/or 210-230. Each of these heterogeneous devices may be coupled to server 460. For example, server 460 may be any of the servers 110, 250, and/or 260. Using the shared interfaces 120 and 170 as well as the services 131-142 and/or 174, and/or the applications 172 in each of the heterogeneous devices, coordinated motion system 400 may implement coordinated motion consistent with the processes of method 300.

In some embodiments, coordinated motion system 400 may include other heterogeneous and/or movable devices that are not shown. In some examples, the other heterogeneous and/or movable devices may include one or more PACS stations, computer-assisted interventional devices, focal interventional devices, localization devices, positioning devices, monitoring devices, smart floors or walls, cameras, range sensors, environment sensors, and/or the like.

Several exemplary uses of the processes of method 300 are now presented to demonstrate how coordinated motion may be implemented in a system with one or more shared interfaces and associated services.

Example 1

Use of follow-me tokens: During a surgery or other procedure it is generally undesirable to undock the articulated arms 425 of the computer-assisted surgical device 420 from a patient until the surgery or procedure is completed. This helps reduce the likelihood of complications due to infection and/or repeated docking to one or more incision sites. During some surgeries or procedures, it may be desirable to change the location, position, and/or height of surgical table 410 while the articulated arms 425 are docked to the patient. To support this, method 300 could be used by surgical table 410 to request a master follow-me token using process 315. Following negotiation through the shared interface of server 460 and token service 137, surgical table 410 could be issued a master follow-me token and computer-assisted surgical device 420 could be issued a slave follow-me token using process 320. Surgical table 410 may then use blackboard service 132 to provide a planned path using process 335, which may be forwarded to computer-assisted surgical device 420 by publisher service 133. Based on the planned path of surgical table 410, computer-assisted surgical device 420 may plan and execute a compliant path that permits articulated arms 425 to remain docked with the patient and that does not disturb the positioning of the surgical instruments. In some examples, this may additionally permit continuation of the surgery or procedure even while surgical table 410 is in motion. When computer-assisted surgical device 420 is not able to remain compliant with the slave follow-me token, it may alert surgical table 410 using alert service 136 so that surgical table 410 may stop its motion before any collision or injury to the patient occurs. In some examples, imaging device 440 may additionally be issued a slave collision-avoidance token so that imaging device 440 may plan and execute a path that avoids collision with both surgical table 410 and the patient as well as computer-assisted surgical device 420 and articulated arms 425. In some examples, imaging device 440 may additionally be issued a slave follow-me token so that imaging device 440 may move along with surgical table 410 and computer assisted surgical device 420 in order to keep a target anatomy of the patient in the field of view of the imaging subsystem 445.

Example 2

Use of collision-avoidance tokens: During a surgery or other procedure it is often desirable to take updated images of a patient using imaging device 440. When imaging device 440 is a tomographic imaging device, imaging device 440 generally moves imaging subsystem 445 in a path about the patient. Collision-avoidance tokens may be used in one of two ways to allow imaging device 440 to take an updated image of the patient without requiring computer-assisted surgical device 420 to undock from the patient. In one example, imaging device 440 may be issued a master collision-avoidance token, computer-assisted surgical device 420 may be issued a slave collision-avoidance token, and surgical table may be issued no movement token. Imaging device 440 may then share a planned path that computer-assisted surgical device 420 may use to plan a corresponding collision avoidance path that allows computer-assisted surgical device 420 to remain docked with the patient. In some examples, the planned path shared by imaging device 440 may include positioning and/or path data associated with one or more energy beams and/or one or energy fields being manipulated by imaging device 440. In another example, the tokens may be reversed with the computer-assisted surgical device 420 receiving the master token and imaging device 440 receiving the slave token. In this case, imaging device 440 may plan an imaging trajectory around the planned path and/or shared position of computer-assisted surgical device 420 and its articulated arms 425. When either the computer-assisted surgical device 420 and/or imaging device 440 cannot comply with the collision-avoidance token it holds, it may alert the other device using alert service 136.

Example 3

Avoidance of surgical personnel and other devices: Motion tracking system 450 may be used to include objects without shared interfaces to participate in coordinated motion. Surgical personnel and the instruments they use may be marked with registration points that may be tracked by motion tracking system 450. Based on the observed registration points, motion tracking system 450 may create one or more virtual movable devices associated with the surgical personnel and instruments. Other movable devices, such as computer-assisted surgical device 420 may avoid those virtual movable devices through the use of collision-avoidance tokens when the virtual movable devices are assigned passive collision-avoidance tokens and act like no-fly zones. In some examples, dimensions of each of the virtual movable devices may be obtained from a database based on the type of the object associated with each registration marker and/or tag. In some examples, when motion tracking system 450 is of RFID type, dimensions of each object can be stored in associated RFID tags and can be retrieved through motion tracking system 450. In some embodiments, computer-assisted surgical device 420 may also hold a slave follow-me token to follow surgical table 410 as described in example 1 above.

Some examples of heterogeneous devices, such as the heterogeneous devices of FIG. 4, and/or coordinated motion system 400 may include non-transient, tangible, machine readable media that include executable code that when run by one or more processors may cause the one or more processors to perform the processes of method 300. Some common forms of machine readable media that may include the processes of method 300 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A medical device comprising:
a movable element
wherein the medical device is configured to:
access services through a shared interface, the services comprising a token service and a data service, the shared interface being shared with a second medical device;
request a movement token from the token service;
receive the movement token from the token service;
receive first data from the data service or transmit first data to the data service, the first data being chosen from one or more of configuration data, kinematic data, and planned motion data;
plan a first motion for the movable element based on the first data and a type of the movement token, wherein the type of the movement token is selected from a group consisting of an exclusive-motion token, a master follow-me token, a slave follow-me token, a master collision-avoidance token, a slave collision-avoidance token, and a passive collision-avoidance token; and
execute the first motion according to the type of the movement token.

2. The medical device of claim 1 wherein the first motion is only executed while the medical device holds the movement token.

3. The medical device of claim 1 wherein the medical device is further configured to output an alarm when the medical device is unable to execute the first motion consistent with the type of the movement token.

4. The medical device of claim 1 wherein the medical device is further configured to perform one or more of:
register with the shared interface;
monitor the shared interface for an alert generated by the second medical device;
receive an alert when a movable object enters or leaves a defined volume;
request a list that indicates any other medical device coupled to the shared interface and holding a specific type of movement token;
request assignment of another movement token to the second medical device; and
keep the movement token until the medical device receives a request to release the movement token.

5. The medical device of claim 1 wherein the medical device is a device selected from a group consisting of a computer-assisted surgical device, a surgical table, an imaging device, a focal interventional device, and a motion tracking system.

6. The medical device of claim 5 wherein:
the medical device is the motion tracking system; and
the medical device is configured to detect and report a location of an object based on one or more registration points;
create a virtual device corresponding to the object; and
transmit kinematic data for the virtual device through the shared interface.

7. The medical device of claim 1 wherein:
the shared services further comprise a blackboard service;
the type of the movement token is the master follow-me token; and
the medical device is further configured to share the planned first motion for the movable element by using the blackboard service.

8. The medical device of claim 1 wherein:
the shared services further comprise a publisher service;
the type of the movement token is the slave follow-me token; and
the medical device is further configured to:
receive a planned second motion for the second medical device from the publisher service; and
plan the first motion for the movable element that is compliant with the planned second motion.

9. The medical device of claim 1 wherein:
the shared services further comprise a blackboard service;
the type of the movement token is the master collision-avoidance token; and
the medical device is further configured to share the planned first motion for the movable element by using the blackboard service.

10. The medical device of claim 1 wherein:
the shared services further comprise a publisher service;
the type of the movement token is the slave collision-avoidance token; and
the medical device is further configured to:
receive a planned second motion for the second medical device from the publisher service; and
plan the first motion for the movable element to avoid a collision with the second medical device.

11. The medical device of claim 1 wherein:
the type of the movement token is the passive collision-avoidance token; and
the medical device is further configured to periodically transmit second data associated with the medical device, the second data being one or more of a current configuration, kinematics, statics, and dynamics of the medical device.

12. The medical device of claim 1 wherein the movable element includes one or more of an articulated arm, an energy beam, and an energy field.

13. The medical device of claim 1 wherein the medical device is further configured to:
send or receive no-fly data or force data through the shared interface; and
plan the first motion further based on the no-fly data, the force data, or on both the no-fly data and the force data;
wherein the force data includes a data element associated with one or more static or dynamic characteristics selected from a group consisting of force, torque, and pressure.

14. A method of coordinated motion, the method comprising:
accessing, by a first device, a shared interface shared with a second device;
requesting a movement token from a token service through the shared interface;
receiving the movement token from the token service;
receiving or transmitting first data through the shared interface, the first data comprising one or more of configuration data, kinematic data, and planned motion data;
planning a first motion for a movable element based on a type of the movement token and the first data, wherein the type of the movement token is selected from a group consisting of an exclusive-motion token, a master follow-me token, a slave follow-me token, a master collision-avoidance token, a slave collision-avoidance token, and a passive collision-avoidance token; and
executing the first motion according to the type of the movement token.

15. The method of claim 14 wherein executing the first motion occurs only while the first device holds the movement token.

16. The method of claim 14, further comprising outputting an alarm when the first motion consistent with the movement token cannot be executed.

17. A coordinated motion system, the system comprising:
- a server comprising a shared interface and a plurality of services accessed through the shared interface, the plurality of services comprising a token service, a publisher service, and a blackboard service;
- a first heterogeneous device coupled to the shared interface and comprising a first movable element; and
- a second heterogeneous device coupled to the shared interface and comprising a second movable element;
- wherein the first heterogeneous device is configured to:
  - request a first movement token from the token service;
  - receive the first movement token from the token service;
  - receive first data from the publisher service, the first data comprising one or more of configuration data, kinematic data, and planned motion data for the second movable element;
  - plan a first motion for the first movable element based on a type of the first movement token and the first data, wherein the type of the first movement token is selected from a group consisting of an exclusive-motion token, a master follow-me token, a slave follow-me token, a master collision-avoidance token, a slave collision-avoidance token, and a passive collision-avoidance token; and
  - execute the first motion according to the type of the first movement token; and
- wherein the second heterogeneous device is configured to:
  - request a second movement token from the token service, wherein a type of the second movement token is selected from a group consisting of an exclusive-motion token, a master follow-me token, a slave follow-me token, a master collision-avoidance token, a slave collision-avoidance token, and a passive collision-avoidance token;
  - receive the second movement token from the token service;
  - transmit the first data to the shared interface using the blackboard service; and
  - release the second movement token.

18. The system of claim 17 wherein:
- the type of the first movement token is the slave follow-me token;
- the type of the second movement token is the master follow-me token; and
- the first motion moves the first movable element in compliance with the first data.

19. The system of claim 17 wherein:
- the type of the first movement token is the slave collision-avoidance token;
- the type of the second movement token is the master collision-avoidance token; and
- the first motion moves the first movable element to avoid collision with the second movable element.

* * * * *